(12) United States Patent
Mudge et al.

(10) Patent No.: US 11,478,611 B2
(45) Date of Patent: Oct. 25, 2022

(54) DELIVERY SYSTEM AND METHOD OF ASSEMBLING SUCH

(71) Applicant: Strait Access Technologies Holdings (Pty) Ltd, Cape Town (ZA)

(72) Inventors: Edward Charles Mudge, Oranjezicht (ZA); Preyen Agasthian Perumall, Gardens (ZA); Deon Bezuidenhout, Cape Town (ZA); Peter Paul Zilla, Cape Town (ZA); Roman Gottardi, Vienna (AT)

(73) Assignee: Strait Access Technologies Holdings (Pty) Ltd, Cape Town (ZA)

( * ) Notice: Subject to any disclaimer, the term of this patent is extended or adjusted under 35 U.S.C. 154(b) by 283 days.

(21) Appl. No.: 16/640,781

(22) PCT Filed: Aug. 28, 2018

(86) PCT No.: PCT/ZA2018/050049
§ 371 (c)(1),
(2) Date: Feb. 21, 2020

(87) PCT Pub. No.: WO2019/060930
PCT Pub. Date: Mar. 28, 2019

(65) Prior Publication Data
US 2021/0008340 A1    Jan. 14, 2021

(30) Foreign Application Priority Data

Sep. 19, 2017    (GB) ...................................... 1715058

(51) Int. Cl.
*A61M 25/01*    (2006.01)
*A61M 25/10*    (2013.01)
(Continued)

(52) U.S. Cl.
CPC .... *A61M 25/0119* (2013.01); *A61M 25/0074* (2013.01); *A61M 25/10* (2013.01); *A61M 2025/0681* (2013.01)

(58) Field of Classification Search
CPC ...... A61F 2/962; A61F 2/966; A61M 25/0119
See application file for complete search history.

(56) References Cited

U.S. PATENT DOCUMENTS 4,946,440 A    8/1990  Hall
5,007,919 A *  4/1991  Silva ............... A61M 25/10184
                                                604/920
(Continued)

FOREIGN PATENT DOCUMENTS

EP    2236168 A2    10/2020
WO    2010001405 A1    1/2010

OTHER PUBLICATIONS

Written Opinion and International Search Report dated Nov. 30, 2018 in International Application No. PCT/ZA2018/050049.

*Primary Examiner* — Elizabeth Houston
*Assistant Examiner* — Lindsey Bachman
(74) *Attorney, Agent, or Firm* — Haugen Law Firm PLLP

(57) ABSTRACT

A catheter delivery system (10) includes: (i) an introducer sheath (12); (ii) a catheter (14) disposed at least partially within the introducer sheath and movable axial along the introducer sheath; (iii) an invaginating tube (16) sealably secured at or near a first axial end (16a) of the invaginating tube to the introducer sheath at or near a first axial end (12 a) of the introducer sheath; (iv) a runner (28) slidably connected to the catheter; (v) the invaginating tube being sealably secured at or near a second axial end (16b) of the invaginating tube to the runner, such that the runner with invaginating tube secured thereto is sealably connected to the catheter and movable axially along at least a portion of (Continued)

the catheter; and (vi) means for pressurising the annular space defined between the introducer sheath, the catheter and the invaginating tube.

15 Claims, 4 Drawing Sheets

(51) Int. Cl.
*A61M 25/06* (2006.01)
*A61M 25/00* (2006.01)

(56) References Cited

U.S. PATENT DOCUMENTS

| | | | |
|---|---|---|---|
| 5,364,345 | A | 11/1994 | Bacich et al. |
| 6,039,721 | A | 3/2000 | Johnson et al. |
| 6,200,288 | B1 | 3/2001 | Adams et al. |
| 6,569,182 | B1 | 5/2003 | Balceta et al. |
| 7,967,798 | B2 | 6/2011 | Foushee et al. |
| 8,435,279 | B2 * | 5/2013 | Beyerlein ................ A61F 2/966 |
| | | | 623/1.11 |
| 2003/0176910 | A1 * | 9/2003 | Vrba .......................... A61F 2/95 |
| | | | 623/1.11 |
| 2008/0125772 | A1 * | 5/2008 | Stone ................. A61B 18/1206 |
| | | | 606/41 |
| 2011/0152760 | A1 | 6/2011 | Parker |
| 2011/0257720 | A1 * | 10/2011 | Peterson ................ A61F 2/966 |
| | | | 623/1.11 |
| 2016/0235478 | A1 | 8/2016 | Bonneau et al. |

\* cited by examiner

DELIVERY SYSTEM AND METHOD OF ASSEMBLING SUCH

BACKGROUND

The present invention relates to a delivery system. More specifically, the present invention relates to an introducer sheath with catheter and an invaginating tube that is: (i) sealed to the introducer sheath at or near a first axial end of the invaginating tube; and (ii) slidable sealed to the catheter at or near a second axial end of the invaginating tube.

The present invention further relates to a method of manufacturing such introducer sheath with catheter.

Various catheters and introducer sheaths with invaginating tubes are known. For instance:

U.S. Pat. No. 6,039,721 "Method and catheter system for delivering medication with an everting balloon catheter", U.S. Pat. No. 5,364,345 "Method of tubal recanalization and catheter system therefor", U.S. Pat. No. 4,946,440 "Evertible membrane catheter and method of use" and US2016/0235478 "Basket and everting balloon with simplified design and control" describe a catheter comprising:

an outer tube;
an inner tube disposed within the outer tube and movable axially relative to the outer tube;
a filament disposed within the inner tube and axially movable relative to the outer and inner tubes;
an invaginating tube connected at its axial ends to a first axial end of the outer tube and to a first axial end of the inner tube, respectively; and
means for pressurising the annular gap defined between the outer tube, the inner tube and the invaginating tube,
wherein movement of the first axial end of the inner tube towards and beyond the first axial end of the outer tube causes the invaginating tube to protrude from the first axial end of the outer tube, and wherein a first axial end of the filament that protrudes from the first axial end of the outer tube is radially compressed by the invaginating tube as the filament and inner tube are simultaneously retracted into the outer tube, in a direction from the first towards the second axial end of the outer tube.

A drawback of these devices is that the inner tube occupies a significant amount of space within the outer tube, limiting the radial dimension of the filament relative to the diameter of the outer tube.

It is also known for an everting toroid device to be slidably mounted to a catheter. Such devices are described in U.S. Pat. No. 6,200,288 "Everting toroid device for insertion into a body cavity".

A drawback of such toroid devices is that everting of the toroid is not easily controlled, and everting of the toroid imposes material drag to relative axial movement of a catheter and its outer sheath.

Furthermore, U.S. Pat. No. 6,569,182 "Introducer/dilator with balloon protection and methods of use" describes an introducer sheath with an internal, axially movable catheter, and an invaginating tube sealed at its axial ends to a first axial end of the introducer sheath and to a first axial end of the catheter, respectively. Similar arrangements are described in US2011/0152760 "Deployment and dilation with an expandable roll sock delivery system".

A drawback of these arrangements is that, since the invaginating tube is not slidably connected to the catheter, relative axial movement of the catheter and introducer sheath is limited by the axial length of the invaginating tube.

Finally, U.S. Pat. No. 7,967,798 "introducer apparatus with eversible sleeve" describes an introducer comprising:

inner and outer concentric tubes that are axially movable relative to each other; and
an invaginating tube that is fixed at a first axial end to a first axial end of the outer tube and extends axially into the inner tube via a first axial end of the inner tube,
wherein the second axial end of the invaginating tube is not secured to either the outer or the inner tube, such that when the first axial end of the inner tube protrudes beyond the first axial end of the outer tube, the invaginating tube similarly protrudes beyond the first axial end of the outer tube to cover the protruding outer radial wall of the inner tube.

A drawback of this arrangement is that protrusion of the first axial end of the inner tube beyond the first axial end of the outer tube is effectively limited by the axial length of the invaginating tube. Furthermore, the invaginating tube does not act radially to compress the inner tube upon retraction of the first axial end of the inner tube within the outer tube.

It is an object of the present invention to provide a delivery system including an introducer sheath a catheter and an invaginating tube extending there between, wherein: (i) protrusion of a first axial end of the catheter beyond a first axial end of the introducer sheath is not limited by the axial length of an invaginating tube extending between the introducer sheath and the catheter; (ii) the invaginating tube acts radially to compress the catheter upon retraction of the first axial end of the catheter within the introducer sheath; and (iii) the radial dimension of the catheter relative to the diameter of the outer tube is not limited by the presence of an intermediate tube.

SUMMARY OF THE INVENTION

According to a preferred embodiment of a first aspect of the invention, there is provided a delivery system that includes:

an introducer sheath;
a catheter disposed at least partially within the introducer sheath and movable axial along the introducer sheath;
an invaginating tube sealably secured at or near a first axial end of the invaginating tube to the introducer sheath at or near a first axial end of the introducer sheath;
a runner slidably connected to the catheter;
the invaginating tube being sealably secured at or near a second axial end of the invaginating tube to the runner, such that the runner with inavaginating tube secured thereto is sealably connected to the catheter and movable axially along at least a portion of the catheter; and
means for pressurising the annular space defined between the introducer sheath, the catheter and the invaginating tube.

Typically, the runner is made of a material that is different to the material from which the invaginating tube is made.

Generally, the delivery system further includes an inflatable balloon on the catheter.

Preferably, the delivery system further includes a limiter on the catheter, and wherein:

the inflatable balloon is disposed between a first axial end of the catheter and the limiter;
the runner is disposed between a second axial end of the catheter and the limiter; and
the limiter limits movement of the runner axially along the catheter.

Optionally, the limiter is a collar that is securable to the catheter. Typically, the limiter is a protrusion that extends radially outwards from the radial surface of the catheter along which the runner, in use, moves by between 15% and 75% of the outer diameter of the catheter in the region along which the runner, in use, moves.

Generally, the catheter is movable between:
an extended condition, in which:
the first axial end of the catheter;
the inflatable balloon; and
the limiter; and
at least a portion of the invaginating tube;
protrudes beyond the first axial end of the introducer sheath; and
a retracted condition, in which:
the inflatable balloon;
the limiter; and
the invaginating tube,
are wholly received within the introducer sheath.

Preferably, the invaginating tube is secured to the introducer sheath in a region of the introducer sheath spaced between 1 mm and 15 mm from the first axial end of the introducer sheath.

Typically, the delivery system further includes a tip secured to the first axial end of the catheter, wherein the tip comprises:
a neck that is between 2 mm and 10 mm in axial length and is sized and shaped to be received within the introducer sheath via the first axial end of the introducer sheath; and
a head that defines a domed portion, which head is oversized relative to the bore defined by the introducer sheath at the first axial end of the introducer sheath, such that the head protrudes from the first axial end of the introducer sheath when the catheter is in the retracted condition.

Generally, the runner comprises at least one o-ring, and wherein the invaginating tube is bonded to the runner.

Preferably, the runner is overmoulded with the invaginating tube.

Typically, the runner has a radial wall thickness of between 3% and 35% of the catheter outer diameter.

Generally, the runner has an inner diameter of between 3.1 mm and 3.3 mm.

Preferably, the radially outer surface of the invaginating tube (before invagination) is bonded:
at the first axial end of the invaginating tube to the radially inner surface of the introducer sheath; and
at the second axial end of the invaginating tube to the runner.

Typically, a portion of the catheter extending from the limiter at least 150 mm towards the second axial end of the catheter defines a right circular cylindrical radial outer surface.

Generally, the invaginating tube (before invagination) is right circular cylindrical with an inner diameter greater than the outer diameter of both: the runner; and the right circular cylindrical portion of the catheter that extends from the limiter towards the second axial end of the catheter.

Preferably, the delivery system further includes a resilient ballast disposed between, and in fluid communication with:
the pressurising means; and
the annular space defined between the introducer sheath, the catheter and the invaginating tube,
wherein, as the catheter moves from the extended condition to the retracted condition, variations in volume within the annular space defined between the introducer sheath, the catheter and the invaginating tube is attenuated by a variation in volume of the resilient ballast, thereby operatively maintaining a pressure within a range of +−30% of nominal operating pressure.

Typically, the invaginating tube is made of Nylon, PEBAX® 50 to 75D hardness, Polyethylene Terephthalate or Urethane.

Generally, the invaginating tube defines at least three helical, equi-angularly offset fold lines extending along the axial length of the invaginating tube.

According to a second aspect of the invention, there is provided a method of assembling a delivery system, which method includes the steps of:
locating a cylindrical runner radially over a mandrel;
locating a second axial end of an invaginating tube radially over the runner;
covering the portion of the invaginating tube that is located radially over the runner with a heat-shrink material;
heating the heat-shrink material and the portion of the invaginating tube that is located radially over the runner to radially compress and mould the invaginating tube to the runner;
removing: the heat-shrink material from the invaginating tube; and the runner from the mandrel;
sealingly securing a first axial end of the invaginating tube to or near a first axial end of the introducer sheath; and
inserting a second axial end of a catheter: axially through the runner; and axially into the introducer sheath via the first axial end of the introducer sheath; and
causing the second axial end of the catheter to protrude beyond the second axial end of the introducer sheath and connecting a pressurising means to the catheter.

Typically, the method further includes the step of invaginating the second axial end of the invaginating tube before locating the second axial end of the invaginating tube radially over the runner.

Generally, the radial outer surface of the first axial end of the invaginating tube is sealingly connected to the radial inner surface of the introducer sheath within a region of the introducer sheath spaced between 1 mm and 15 mm from the first axial end of the introducer sheath.

Typically, the method further includes the step of forming at least three equi-angularly offset helical creases along the length of the invaginating tube.

BRIEF DESCRIPTION OF THE DRAWINGS

The invention will now be described in more detail, by way of example only, with reference to the accompanying drawings in which:

FIG. 2b is a side diametric cross-sectional view of a delivery system showing an alternative arrangement for securing an invaginating tube to a runner;

DESCRIPTION OF THE INVENTION

Figure 1:
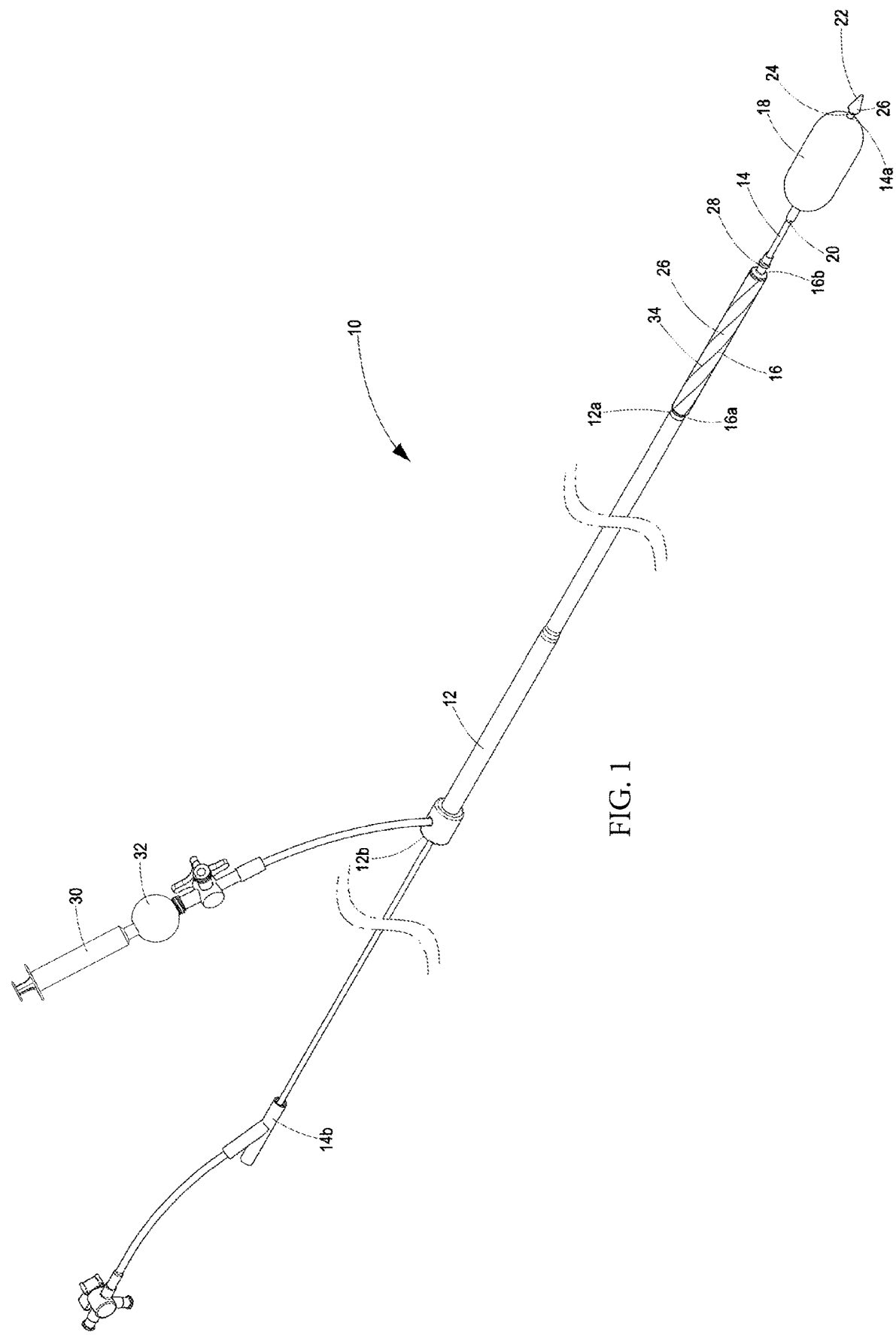
FIG. 1 is a perspective view of a delivery system according to a preferred embodiment of the invention, with a catheter in an extended condition.

With reference to FIGS. 1 to 4 of the drawings, a delivery system 10 includes an introducer sheath 12, a catheter 14 and an invaginating tube 16.

The introducer sheath 12 is a cylindrical tube that provides access to a patient's artery (typically femoral artery) during a surgery. The introducer sheath 12 has a first axial end 12a and a second axial end 12b and defines a bore with a diameter between 1 mm and 12 mm.

The catheter 14 is a flexible cylindrical tube defining a first axial end 14a and a second actual end 14b. An inflatable balloon 18 is mounted to the catheter 14 near the first axial end 14a of the catheter 14. A limiter 20 extends radially outwards from the radial peripheral surface of the catheter 14 near the axial end of the inflatable balloon 18 distal the first axial end 14a of the catheter 14. The limiter 20 preferably extends radially outwards from the radial peripheral surface of the catheter 14 by between 15% and 75% of the outer diameter of the catheter (i.e. in the region along which the runner 28, in use, moves). Optionally, the limiter comprises a collar that is securable to the catheter, around the radial outer surface of the catheter. A portion of the catheter 14 extending from the limiter 20 at least 50 mm towards the second axial end 14b of the catheter 14 is right circular cylindrical with an outer diameter of 3.2 mm. A tip 22 is secured to the first axial end 14a of the catheter 14. The tip 22 comprises a cylindrical neck 24 terminating in an enlarged head 26. The cylindrical neck 24 is between 2 mm and 10 mm in axial length and between 2.5 mm and 6 mm in diameter, i.e. sized and shaped to be received within the bore defined by the introducer sheath 12 via the first axial and 12a of the introducer sheath 12. The enlarged head 26 is either dome-shaped or conical, between 5 mm and 50 mm in axial length. The diameter of the enlarged head's base is between 3 mm and 7 mm in diameter, i.e. oversized relative to the bore defined by the introducer sheath 12.

The catheter 14 extends through the bore defined by the introducer sheath 12, with the second axial end 14b of the catheter 14 protruding from the second axial end 12b of the introducer sheath 12.

The invaginating tube 16 is made of a flexible material, such as Nylon 12, PEBAX® 50 to 75D hardness, Polyethylene Terephthalate or Urethane. Prior to invagination, the invaginating tube 16 initially comprises a right circular cylindrical tube: between 4 mm and 10 mm in outer diameter; between 50 mm and 100 mm in axial length; and between 20 micron and 150 micron in radial wall thickness. The inner diameter of the invaginating tube 16 is greater than the diameter of the right circular cylindrical portion of the catheter 14 extending from the limiter 20. A second axial end 16b of the invaginating tube 16 is invaginated inwards (i.e. the second axial end 16b of the invaginating tube 16 is deformed radially inwards and axially along the invaginating tube 16).

A first axial end 16a of the invaginating tube 16 is sealably secured to the introducer sheath 12 at or near the first axial end 12a of the introducer sheath 12. More specifically, the first axial end 16a of the invaginating tube 16 is sealed to the inner radial surface of the introducer sheath 12 in a region of the introducer sheath 12 spaced between 1 mm and 15 mm from the first axial 12a end of the introducer sheath 12. This spacing from the first axial end 14a of the catheter 14 corresponds to the axial length of the neck 24 of the catheter tip 22.

The phrases:

"secured near a first axial end 12a of the introducer sheath 12" is intended to mean "a distance from the first axial end 12a of the introducer sheath 12 no greater than 11 mm"; and "secured near a first axial end 16a of the invaginating tube 16" is intended to mean "a distance from the first axial end 16a of the invaginating tube 16 no greater than 11 mm".

A runner 28 in the form of a single, or preferably a pair of axially spaced o-rings is slidably connected to the catheter 14. More specifically, the o-rings extend around the catheter 12 in the right circular cylindrical portion of the catheter 14 that extends from the limiter 20 towards the second axial end 14b of the catheter 14. The o-rings have: an internal diameter between 3.1 mm and 3.3 mm to create a seal between the o-rings and the catheter 14; and a radial wall thickness of between 3% and 35% of the catheter shaft 14 outer diameter. The inner diameter of the invaginating tube 16 (before invagination) is greater than the outer diameter of the runner 28. The runner 28 is slidable along the right circular cylindrical portion of the catheter 14, with the limiter 20 limiting further travel of the runner 28 towards the first axial end 14a of the catheter 14.

The runner 28 is made of a material (e.g. silicone, high density polyethylene, fluorinated ethylene propylene) that is different to the material from which the invaginated tube 16 is made.

It will be appreciated that, although the runner 28 has been described as a pair of o-rings, the runner 28 could alternatively be a cylindrical tube.

It will also be appreciated that, although the limiter 20 has been described as a radial protrusion, the limiter 20 could be any other formation or feature that limits travel of the runner 28 along the catheter 14 towards the first axial end 14a of the catheter 14. For example, the limiter 20 could be a region with a high coefficient of friction or even an indentation within which the runner 28 is captured.

The second axial end 16b of the invaginated tube 16 radially overlies the runner 28 and is bonded thereto. In other words, the runner 28 is overmolded by the second axial end 16b of the invaginated tube 16. With the first axial end 16a of the invaginated tube 16 sealed to the introducer sheath 12 and the second axial end 16b of the invaginated tube 16 sealed (via the runner 28) to the catheter 14, the introducer sheath 12, invaginating tube 16 and catheter 14 define an annular space there between.

A means for pressurising the annular space defined between the introducer sheath 12, the catheter 14 and the invaginating tube 16 is provided in the form of a syringe 30. By pressurising this annular space, the invaginating tube 16 is more resistant to buckling when subjected to compressive forces imposed by the introducer sheath 12 and the catheter 14.

The catheter 14 is movable between:
- an extended condition (shown in FIGS. 1 and 2), in which:
  - the first axial end 14a of the catheter 14;
  - the inflatable balloon 18; and
  - the limiter 20; and
  - at least a portion of the invaginating tube 16;

protrudes beyond the first axial end 12a of the introducer sheath 12; and
- a retracted condition (shown in FIG. 4), in which:
  - the inflatable balloon 18;
  - the limiter 20; and
  - the invaginating tube 16, are wholly received within the introducer sheath 12.

Figure 3:
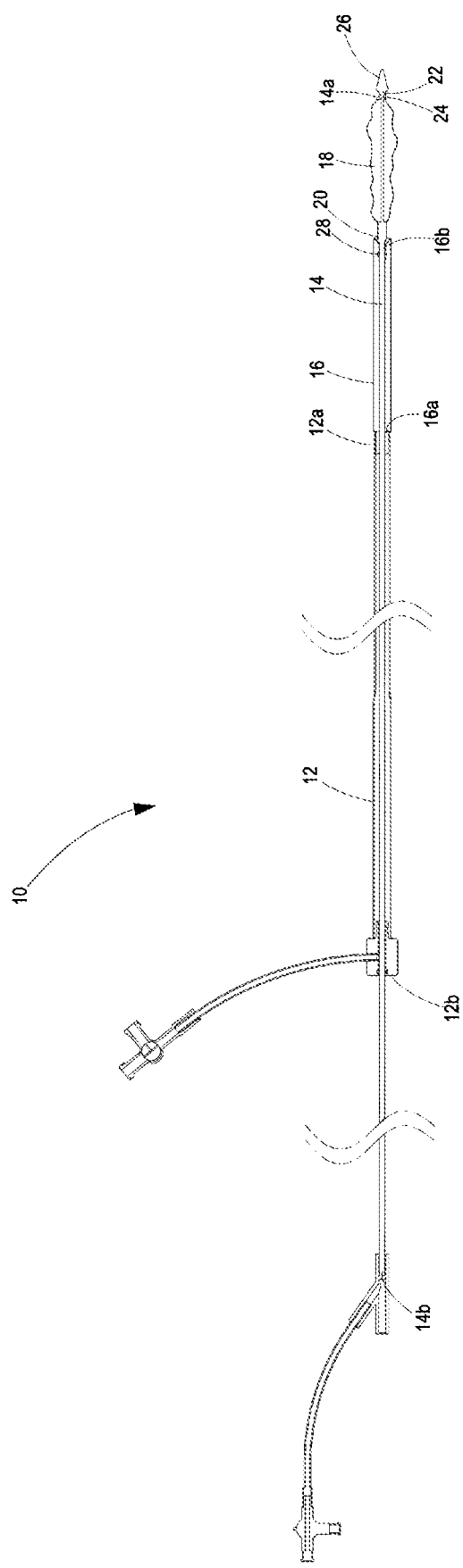
FIG. 3 is a side diametric cross-sectional view of the delivery system in FIG. 1, with the catheter in an intermediate position.
Figure 4:
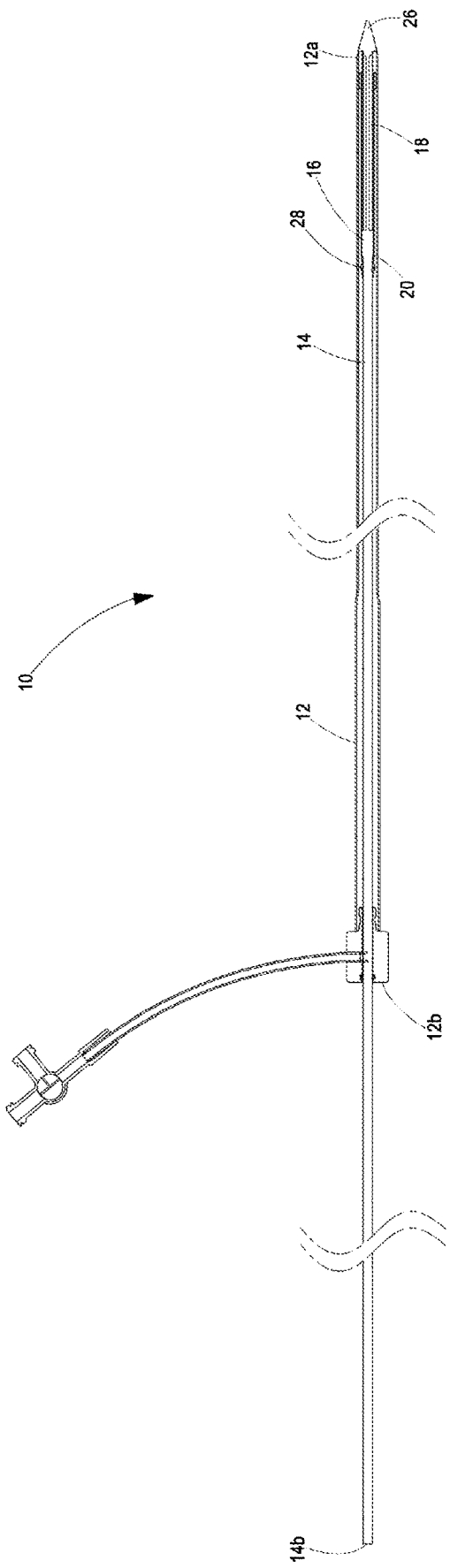
FIG. 4 is a side diametric cross-sectional view of the delivery system in FIG. 1, with the catheter in a retracted condition.

As the catheter 14 is moved from the extended condition to the retracted condition, the runner 28 slides along the catheter 14, towards the first axial end 14a of the catheter. When the runner 28 contacts the limiter 20, further movement of the runner 28 along the catheter 14 is resisted. Continued retraction of the catheter 14 within the introducer sheath 12 subjects the invaginating tube 16 to compressive forces that induce further invagination of the invaginating tube 16, thereby enveloping the inflatable balloon 18 by the invaginating tube 16. This position of the catheter 14 is referred to as an intermediate position and is shown in FIG. 3. It will be appreciated that pressurisation by the syringe 30 of the annular space defined between the introducer sheath 12, the catheter 14 and the invaginating tube 16 assists the invaginating tube 16 to resist buckling when subjected to such compression forces. Enveloping of the inflatable balloon 18 by the invaginating tube 16 imposes a radially inwards compressive force on the inflatable balloon 18. Such radial compression of the inflatable balloon 18 (caused by continuing retraction of the catheter from the intermediate positions to the retracted condition) also induces variations in volume within the annular space defined between the introducer sheath 12, the catheter 14 and the invaginating tube 16. To attenuate such pressure variations to within an operative range between 0.5 atmospheres and 6 atmospheres, a resilient ballast 32, in the form of a flexible tube is disposed between: the annular space defined between the introducer sheath 12, the catheter 14 and the invaginating tube 16 on the one hand; and the syringe 30 on the other hand. The resilient ballast 32 expands radially, increasing in volume, during pressure peaks, and contracts radially, decreasing in volume, during pressure troughs. The ballast 32 is preferably designed operatively to maintain a pressure within a range of +–30% of nominal operating pressure.

Figure 2:
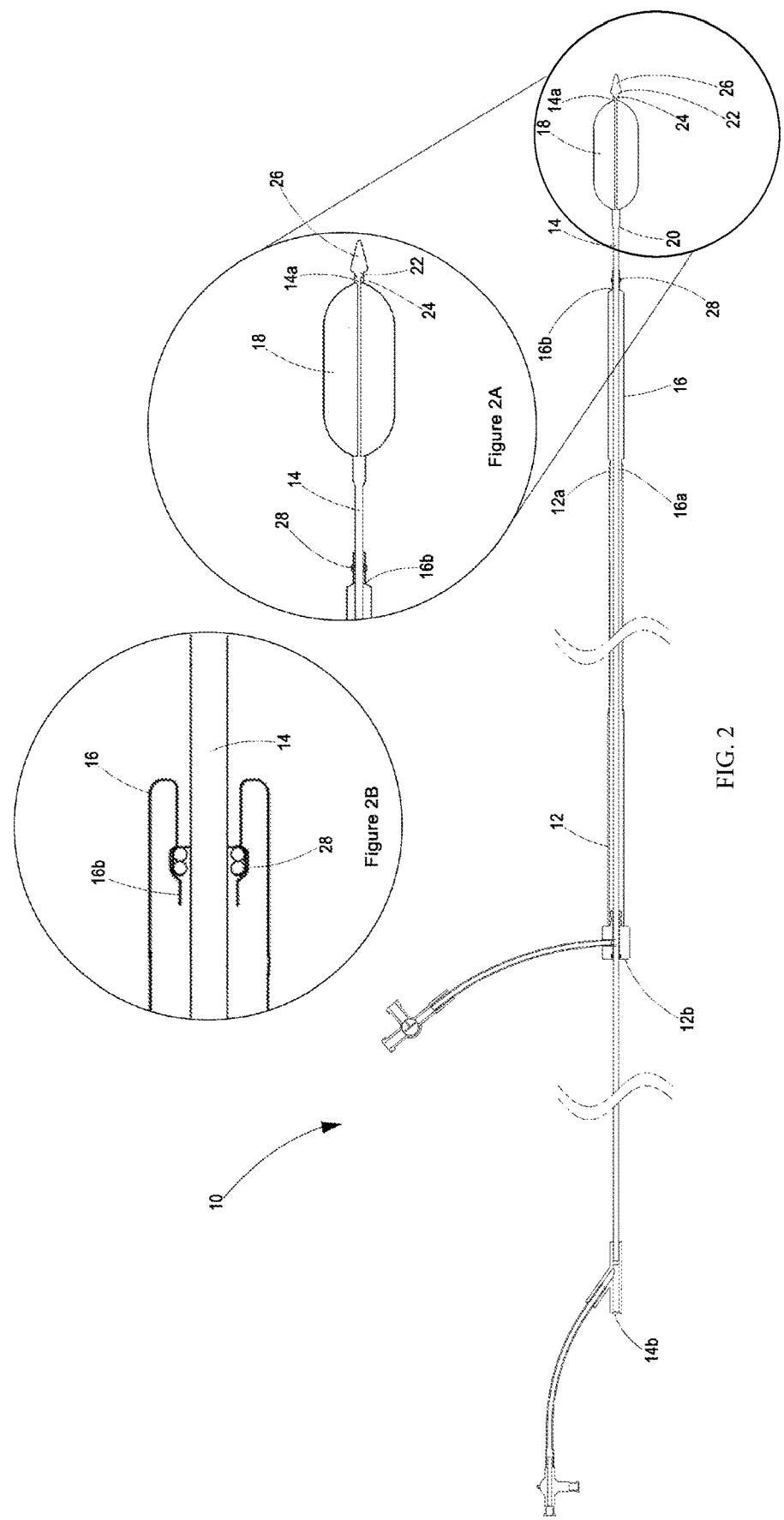
FIG. 2 is a side diametric cross-sectional view of the delivery system in FIG. 1, with the catheter in the extended condition.

With particular reference to FIGS. 1 and 2, the invaginating tube 16 defines at least three helical, equi-angularly offset fold lines 34 extending along the axial length of the invaginating tube 16. The Figures show four equi-angularly offset fold lines 34. These fold lines facilitate invaginating of the invaginating tube 16 as the catheter 14 is moved from the extended condition to the retracted condition.

By enveloping, invaginating and radially compressing the inflatable balloon 18, the invaginating tube 16 facilitates retraction of the inflatable balloon 18 within the introducer sheath 12.

When the catheter 14 is in the retracted condition, the neck 24 of the catheter tip 22 is received within the introducer sheath 12 via the first axial end 12a of the introducer sheath 12, while the enlarged head 26 of the catheter tip 22 abuts but protrudes from the first axial end 12a of the introducer sheath 12a.

It will be appreciated that, although the delivery system 10 has been described with the invaginated second axial end 16b of the invaginated tube 16 secured to the runner 28, the inner radial surface of the tube 16 (before invagination) could alternatively be bonded to the runner 28.

We now turn to describing a method of assembling the delivery system 10. The method includes the steps of:

Locating a cylindrical runner 28 radially over a mandrel (not shown).

(Optionally) forming at least three equi-angularly offset helical creases 34 along the length of the invaginating tube 16.

(Optionally) invaginating the second axial 16b end of the invaginating tube 16 (as shown in FIG. 2b).

Locating a second axial end 16b of an invaginating tube 16 radially over the runner 28.

FIG. 2 shows the preferred arrangement with the radially outer surface of the invaginating tube 16 (before invagination) is bonded: (i) at the first axial end 16a of the invaginating tube 16 to the radially inner surface of the introducer sheath 12; and (ii) at the second axial end 16b of the invaginating tube 16 to the runner 28.

Covering the portion of the invaginating tube 16 that is located radially over the runner 28 with a heat-shrink material (not shown).

Heating the heat-shrink material and the portion of the invaginating tube 16 that is located radially over the runner 28 to radially compress and mould the invaginating tube 16 to the runner 28.

Removing: the heat-shrink material from the invaginating tube 16; and the runner 28 from the mandrel.

Sealingly securing a first axial end 16a of the invaginating tube 16 to or near a first axial end 12a of the introducer sheath 12, such that the radial outer surface of the first axial end of the invaginating tube 16 is sealingly connected to the radial inner surface of the introducer sheath 12 within a region of the introducer sheath 12 spaced between 1 mm and 15 mm from the first axial 12a end of the introducer sheath 12.

Inserting a second axial end 14b of a catheter 14: axially through the runner 28; and axially into the introducer sheath 12 via the first axial end 12a of the introducer sheath 12.

Causing the second axial end 14b of the catheter 14 to protrude beyond the second axial end 12b of the introducer sheath 12 and connecting a pressurising means 30 to the catheter 14 or introducer sheath.

The invention claimed is:

1. A delivery system including:

an introducer sheath;

a catheter disposed at least partially within the introducer sheath and movable axially along the introducer sheath;

a device on the catheter; and an invaginating tube sealably secured at or near a first axial end of the invaginating tube to the introducer sheath at or near a first axial end of the introducer sheath;

a runner slidably connected to the catheter;

the invaginating tube being sealably secured at or near a second axial end of the invaginating tube to the runner, such that the runner with invaginating tube secured thereto is sealably connected to the catheter and movable axially along at least a portion of the catheter; and means for pressurising the annular space defined between the introducer sheath, the catheter and the invaginating tube;

the catheter being movable between:

(i) an extended condition, in which:

a first axial end of the catheter;

the device; and at least a portion of the invaginating tube, protrudes beyond the first axial end of the introducer sheath; and (ii) a retracted condition, in which:

the device; and the invaginating tube, are wholly received within the introducer sheath, wherein the invaginating tube and device are configured such that, as the catheter is moved from the extended condition to the retracted condition, the invaginating tube envelopes at least a portion of the device, imposing a radially inwards compressive force on the device, thereby radially to compress the device.

2. A delivery system according to claim 1, wherein the runner is made of a material that is different to the material from which the invaginating tube is made.

3. A delivery system according to claim 1, wherein the device is an inflatable balloon.

4. A delivery system according to claim 3, further including a limiter on the catheter, and wherein:
the inflatable balloon is disposed between the first axial end of the catheter and the limiter;
the runner is disposed between a second axial end of the catheter and the limiter; and
the limiter limits movement of the runner axially along the catheter.

5. A delivery system according to claim 4, wherein the limiter is a collar that is securable to the catheter.

6. A delivery system according to claim 4, wherein the limiter is a protrusion that extends radially outwards from the radial surface of the catheter by between 15% and 75% of an outer diameter of a region of the catheter along which the runner, in use, moves.

7. A delivery system according to claim 6, wherein the invaginating tube is secured to the introducer sheath in a region of the introducer sheath spaced between 1 mm and 15 mm from the first axial end of the introducer sheath.

8. A delivery system according to claim 7, further including a tip secured to the first axial end of the catheter, wherein the tip comprises:
a neck that is between 2 mm and 10 mm in axial length and is sized and shaped to be received within the introducer sheath via the first axial end of the introducer sheath; and
a head that defines a domed portion, which head is oversized relative to the bore defined by the introducer sheath at the first axial end of the introducer sheath, such that the head protrudes from the first axial end of the introducer sheath when the catheter is in the retracted condition.

9. A delivery system according to claim 8, wherein the runner comprises at least one o-ring, and wherein the invaginating tube is bonded to the runner.

10. A delivery system according to claim 9, wherein:
the runner is overmoulded with the invaginating tube;
the runner has a radial wall thickness of between 3% and 35% of the catheter outer diameter; and
the runner has an inner diameter of between 3.1 mm and 3.3 mm.

11. A delivery system according to claim 10, wherein the radially outer surface of the invaginating tube, before invagination, is bonded:
at the first axial end of the invaginating tube to the radially inner surface of the introducer sheath; and
at the second axial end of the invaginating tube to the runner.

12. A delivery system according to claim 11, wherein a portion of the catheter extending from the limiter at least 150 mm towards the second axial end of the catheter defines a right circular cylindrical radial outer surface.

13. A delivery system according to claim 12, wherein the invaginating tube, before invagination, is right circular cylindrical with an inner diameter greater than the outer diameter of both: the runner; and the right circular cylindrical portion of the catheter that extends from the limiter towards the second axial end of the catheter.

14. A delivery system according to claim 13, further including a resilient ballast disposed between, and in fluid communication with:
the pressurising means; and
the annular space defined between the introducer sheath, the catheter and the invaginating tube,
wherein, as the catheter moves from the extended condition to the retracted condition, variations in volume within the annular space defined between the introducer sheath, the catheter and the invaginating tube is attenuated by a variation in volume of the resilient ballast, thereby operatively maintaining a pressure within a range of +−30% of nominal operating pressure.

15. A delivery system according to claim 14, wherein the invaginating tube defines at least three helical, equi-angularly offset fold lines extending along the axial length of the invaginating tube.

* * * * *